(12) United States Patent
Lin et al.

(10) Patent No.: US 11,745,436 B2
(45) Date of Patent: Sep. 5, 2023

(54) LIQUID-IMPERMEABLE STITCHING METHOD FOR SEAM OF VAPOR-PERMEABLE VIRUS-BARRIER FABRIC

(71) Applicant: FOSHAN KING WONDER HI-TECH CO., LTD., Guangdong (CN)

(72) Inventors: Yuwei Lin, Guangdong (CN); Yaogen Wu, Guangdong (CN)

(73) Assignee: FOSHAN KING WONDER HI-TECH CO., LTD., Guangdong (CN)

( * ) Notice: Subject to any disclaimer, the term of this patent is extended or adjusted under 35 U.S.C. 154(b) by 0 days.

(21) Appl. No.: 16/321,388

(22) PCT Filed: Aug. 8, 2016

(86) PCT No.: PCT/CN2016/093908
§ 371 (c)(1),
(2) Date: Jan. 28, 2019

(87) PCT Pub. No.: WO2018/018653
PCT Pub. Date: Feb. 1, 2018

(65) Prior Publication Data
US 2019/0168465 A1 Jun. 6, 2019

(30) Foreign Application Priority Data
Jul. 27, 2016 (CN) .................. 201610601282.X (51) Int. Cl.
*B29C 65/00* (2006.01)
*B32B 7/12* (2006.01)
(Continued)

(52) U.S. Cl.
CPC ............ *B29C 66/1122* (2013.01); *B32B 7/12* (2013.01); *B32B 27/02* (2013.01); *B32B 27/12* (2013.01);
(Continued)

(58) Field of Classification Search
CPC ..... B29C 66/1122; B29C 65/02; B29C 65/38; B29C 66/91933; B29C 66/91921;
(Continued)

(56) References Cited

U.S. PATENT DOCUMENTS 5,445,874 A * 8/1995 Shehata ................ B32B 27/12
442/287
5,682,618 A * 11/1997 Johnson ............ B29C 66/73921
2/275

(Continued)

FOREIGN PATENT DOCUMENTS

CN 101374651 A 2/2009
CN 202354419 U 8/2012
(Continued)

OTHER PUBLICATIONS

"Material Safety Data Sheet Sontara Spunlaced Fabrics (All Types)" from Dupont Dec. 1998.*
(Continued)

*Primary Examiner* — John L Goff, II
(74) *Attorney, Agent, or Firm* — Hamre, Schumann, Mueller & Larson, P.C.

(57) ABSTRACT

A fluid impervious stitching method for a seam of a vapor-permeable virus-barrier laminate. The laminate comprises: at least one thermoplastic resin fiber layer; at least one vapor-permeable virus-barrier thermoplastic elastomer film layer; and a bonding layer located between the two layers and formed of an adhesive capable of being fused with the two layers. In the stitching method, overlapping or stacking
(Continued)

Overlapping Manner 1 (a Three-layer Structure)

is performed to form a seam, and heat sealing is performed on the laminate at the seam. The temperature of heat sealing is higher than the melting point of a material layer having the highest melting point in the laminate, but lower than the temperature at which perforation or decomposition occurs in any material layer in the laminate. The heat-stitched seam has excellent windproof, vapor-permeable, virus barrier and liquid-barrier performance, has a smooth appearance without wrinkles, and feels soft. Also provided is a protective textile product prepared by means of the stitching method.

8 Claims, 2 Drawing Sheets

(51) Int. Cl.
*B32B 27/12* (2006.01)
*B32B 37/04* (2006.01)
*B32B 37/06* (2006.01)
*B32B 37/10* (2006.01)
*B32B 37/12* (2006.01)
*B32B 37/15* (2006.01)
*B32B 33/00* (2006.01)
*B32B 27/02* (2006.01)

(52) U.S. Cl.
CPC .............. *B32B 33/00* (2013.01); *B32B 37/04* (2013.01); *B32B 37/06* (2013.01); *B32B 37/10* (2013.01); *B32B 37/12* (2013.01); *B32B 37/15* (2013.01)

(58) Field of Classification Search
CPC ............. B29C 66/919; B29C 66/73115; B29C 66/135; B29C 66/1352; B29C 66/7234; B29C 66/73182; B29C 66/73187; B29C 66/43929; B29C 66/949; B29C 66/73921; B29C 66/43; B32B 37/04; B32B 37/06; B32B 7/12; B32B 27/12; B32B 37/10; B32B 37/12; B32B 37/15; B32B 2437/00; B32B 37/0076; B32B 37/0084; B32B 37/065; B32B 37/30; A41D 2300/52; A41D 13/1209; A41D 27/245; B29L 2031/48
USPC .............................................. 2/51; 156/308.4
See application file for complete search history.

(56) References Cited

U.S. PATENT DOCUMENTS

| | | |
|---|---|---|
| 5,782,191 A | 7/1998 | Wong |
| 7,390,376 B2 | 6/2008 | Palomo et al. |
| 8,513,148 B2 | 8/2013 | Irie et al. |
| 9,005,392 B2 | 4/2015 | Schneider et al. |
| 9,643,390 B2 | 5/2017 | Schneider et al. |
| 10,123,910 B2 | 11/2018 | Schneider et al. |
| 10,123,911 B2 | 11/2018 | Schneider et al. |
| 2001/0039989 A1* | 11/2001 | Waldrop ............... B29C 65/086 156/73.3 |
| 2004/0094265 A1 | 5/2004 | Palomo et al. |
| 2010/0138977 A1* | 6/2010 | Lin ....................... B29C 66/727 2/125 |
| 2013/0177747 A1 | 7/2013 | Lin et al. |
| 2016/0318281 A1 | 11/2016 | Ikoma et al. |

FOREIGN PATENT DOCUMENTS

| | | |
|---|---|---|
| CN | 103192567 A | 7/2013 |
| CN | 104135981 A | 11/2014 |
| CN | 105764967 A | 7/2016 |

OTHER PUBLICATIONS

International Search Report issued for International Patent Application No. PCT/CN2016/093908, dated Apr. 11, 2017, 11 pages including English translation.

* cited by examiner

FIG. 1: Overlapping Manner 1 (a Three-layer Structure)

FIG. 2: Overlapping Manner 2 (a Three-layer Structure)

FIG. 3: Overlapping Manner 3 (a Two-layer Structure)

LIQUID-IMPERMEABLE STITCHING METHOD FOR SEAM OF VAPOR-PERMEABLE VIRUS-BARRIER FABRIC

TECHNICAL FIELD

The present invention relates to a fluid impervious stitching method for a seam of a vapor-permeable and virus-barrier laminate; more specifically, the present invention relates to a heat-stitching method for carrying out heat sealing by means of overlapping or stacking so as to heat seal the seam of a vapor-permeable, virus-barrier and fluid impervious disposable fabric.

BACKGROUND OF THE INVENTION

At present, when a two-layer or multi-layer composite non-woven fabric which is vapor-permeable, virus-barrier and fluid impervious is being manufactured, a suture line or an ultrasonic stitching is conventionally used. However, such techniques are disadvantageous in that the barrier performance of the fabric is weakened, and the suture is prone to crack when subjected to external force. It is thus necessary to provide an alternative stitching technique to guarantee the peeling strength and the barrier performance of the fabric. If stitching is conducted at a temperature lower than the melting point of any of the materials, particularly when the gram weight (the gram per square meter weight) and the thickness of the material are variable, the stitching process tends to be unstable, even results in false suture, unable to maintain a desirable barrier performance. If stitching is conducted at a temperature higher the temperature at which perforation or decomposition occurs in any material layer in the laminate, its barrier performance can not be well guaranteed either. In the art, it is possible to carry out heat stitching at a temperature lower than the temperature of the fluid-impervious layer but higher than the temperature of the cloth layer. However, when the thickness of the film or the manufacturer of the film material changes, the seam of the product often experiences fluid permeation, a decrease in the heat sealing strength, or a failure to pass the virus barrier test ASTM F1671. This has brought tremendous pressure on the technology, market, cost, etc. for the art, threatening the personal safety of product users in particular. Likewise, the continuous distribution of the intermediate glue layer and the type of film is also directly connected to the result of the barrier test and hydrostatic pressure at the heat-stitched seam. In some cases, some full coverage or non-moisture-transmittable film are directly used, which hampers the moisture permeability of the material and results in discomfort of the product user, hindering them from conducting long hours of precision work. For the choice of material of the glue layer, fast aging materials are often used in the market, which causes problems for the barrier performance and shelf life of the seam, resulting in inefficiency and bringing about huge cost pressure due to frequent replacement.

Chinese patent CN 200780003514.0 discloses a heat-adhesive laminated non-woven fabric without a fluid impervious layer. Although it has desirable peeling strength and vapor permeability, it fails to guarantee a long-time effective barrier performance.

Chinese utility model CN 202354419U discloses a method for heat sealing a sleeve, but only a single layer tear-resistant plastic rather than a laminate is used.

U.S. Pat. No. 7,390,376 B2 discloses a heat-stitching method for a seam of a fluid impervious laminate, but its stitching temperature is limited to be lower than or equal to the melting point of the fluid impervious film layer. In the case when the thickness of the fluid impervious film layer is increased to 30 um, or when the material manufacturer changes, or when the surface fabric is non-woven, it may fail to pass the blood-barrier test or the virus-barrier test, and thus unable to meet the needs of the market.

The drawback that conventional seams of fluid impervious laminates may fail to achieve desirable barrier performance plagues the art. Heat stitching method specifically designed for laminates with certain thickness are prone to result in stiff and unstable seams, or conditions for performing stitching are too narrowly specified, which increases stitching cost and technical instability, especially hampering the precision control and stability of equipment and the stable later use of the equipment. Such has brought about enormous economic and social pressures, hindering the development of the art and the promotion of safety and labor protection. Therefore, to overcome such drawbacks has become a pressing demand in relevant industries.

SUMMARY OF THE INVENTION

It is, therefore, one of objects of the present invention to provide a vapor-permeable, moisture transmittable, fluid impervious, and virus-barrier protective textile formed of a thermoplastic elastomer film layer laminate and a heat stitching method for a seam of the laminate.

In order to achieve the above objects, the present invention provides, on one aspect, a stitching method for making a fluid impervious seam at a vapor-permeable and virus-barrier laminate, wherein the laminate comprises a plurality of material layers:

at least one thermoplastic resin fiber layer with a gram weight of 1-500 $g/m^2$, at least one vapor-permeable and virus-barrier thermoplastic elastomer film layer with a thickness of 3-200 μm, and an bonding layer formed between the thermoplastic resin fiber layer and the thermoplastic elastomer film layer, by a glue capable of being fused with the thermoplastic resin fiber layer and the thermoplastic elastomer film layer, the bonding layer having a gram weight of 0.1 $g/m^2$ or more, wherein, in the above stitching method for a seam of a laminate, the laminate is overlapped or stacked to form a seam, and the laminate at the portion of the seam is heat-sealed; and wherein, the temperature of heat sealing is higher than or equal to the melting point of a material layer having the highest melting point in the laminate, but lower than the temperature at which perforation or decomposition occurs in any material layer in the laminate.

Preferably, according to the stitching method for a seam of the present invention, the heat sealing causes all material layers to experience a certain degree of melting.

According to the stitching method for a seam of the present invention, heat sealing may be done by performing thermal-press at the overlapped or stacked portion of the laminate by means of a heat-stitching device to form a suture. In general, the heat sealing can be carried out at a pressure of 0.001 to 1 MPa, more preferably 0.1 to 0.8 MPa, most preferably 0.1 MPa to 0.6 MPa. Preferably, the pressing lasts for 0.01 to 600 s, more preferably for 0.1 to 480 s, most preferably for 1 to 480 s.

According to the stitching method for a seam of a laminate of the present invention, overlapping or stacking is performed to form an overlapping portion of the fabric at the seam, and the heat seal side may be any side, preferably these heat seal sides are of the same material. The temperature of heat sealing is higher than the melting point of a material layer having the highest melting point in the laminate, but lower than the temperature at which perforation or decomposition occurs in any material layer in the laminate; all materials experience a certain degree of melting during heat sealing.

According to the stitching method for a seam of the present invention, the thermal press device used for the heat-stitching may be an ultrasound or high frequency or pulse heat sealing machine, a high temperature heat-sealing machine, or a roller sealing machine and the like.

The heat-stitched seam formed by the stitching method of the present invention is desirable in its peeling strength, and is wind-proof, vapor-permeable, fluid impervious, virus-barrier, water-proof, as well as having a smooth, non-crimple appearance, and soft hand-feel. As to hand-feel test, the elastomer module may be tested under ASTM D828 standard, and softness is tested under ISO 17235-2002. It is desirable to adopt ISO 17235-2002 standard for testing the protective textile product formed by using the above stitching method for a seam, and the larger the obtained value, the softer the hand-feel. The fluid imperviousness, hydrostatic pressure, blood barrier and virus barrier performance, and heat sealing strength are all closely connected to parameters such as the material of each layer of the laminate, its gram weight and the heat-stitching conditions.

On another aspect, for achieving the purpose of the present invention, the present invention also provides a protective textile product using a vapor-permeable and virus-barrier laminate. The protective textile product uses the stitching method for a seam described above to form a fluid impervious seam at the stitched portion of the laminate, wherein the laminate comprises:

at least one thermoplastic resin fiber layer with a gram weight of 1-500 g/m$^2$, preferably of 5-200 g/m$^2$, more preferably of 10-150 g/m$^2$, at least one vapor-permeable and virus-barrier thermoplastic elastomer film layer with a thickness of 3-200 μm, and a bonding layer formed between the thermoplastic resin fiber layer and the thermoplastic elastomer film layer, by the glue which is capable of being fused with the two layers, the gram weight of the bonding layer being more than 0.1 g/m$^2$.

In the present invention, the thickness of the vapor-permeable, virus-barrier thermoplastic elastomer film layer is preferably 4 to 100 μm, more preferably 5 to 90 μm.

In the protective textile product of the present invention, the thermoplastic resin fiber layer may be any fibrous material, preferably a natural fiber fabric and a chemical fiber fabric or a non-woven fabric, such as: fibers of polyester and its derivatives, fibers of polyamide and its derivatives, fibers of polyimide and its derivatives, fibers of polyurethane and its derivatives, fibers of polypropylene and its derivatives, fibers of polyethylene and its derivatives, fibers of polyvinyl alcohol and its derivatives, fibers of polyacrylonitrile and its derivatives, bio-based fibers, degradable fibers and their derivatives, or a textile product made of mixtures thereof.

In the present invention, the material of the thermoplastic resin fiber layer may be a single component or a multi-component material layer, and the material of the thermoplastic resin fiber layer may be a multi-layer co-extrusion or a single-layer extrusion.

In the protective textile product of the present invention, the material of the vapor-permeable and virus-barrier thermoplastic elastomer film layer may be a multi-layer co-extrusion or a single layer extrusion.

In the protective textile product of the present invention, the vapor-permeable and virus-barrier thermoplastic elastomer film layer can be a thermoplastic elastomer plastic and its derivatives and mixtures selected from the group consisting of: polyvinyl acetate and its derivatives and mixtures, polyvinyl chloride and its derivatives and mixtures, polyvinyl alcohol and its derivatives and mixtures, polyethylene terephthalate and its derivatives and mixtures, and polybutylene terephthalate and its derivatives and mixtures, polyamide and its derivatives, amino resin and its derivatives and mixtures, unsaturated polyester resin and its derivatives and mixtures, epoxy resin and its derivatives and mixtures, organic silicone resin and its derivatives and mixtures. More preferable elastomer and its derivatives can be polybutylene terephthalate and its derivatives and mixtures, polyurethane and its derivatives and mixtures, TPO (thermoplastic polyolefin elastomer) and its derivatives and mixtures, TPV (thermoplastic vulcanizates) and its derivatives and mixtures, and the like.

In the protective textile product of the present invention, the glue may be any type of glue, preferably a solvent adhesive, a water-based adhesive, a hot-melt adhesive, and a non-solvent adhesive which are not easily aging. The solvent adhesive includes a reactive glue and a non-reactive glue, preferably a moisture-reactive polyurethane glue, a bi-component polyurethane glue, a siloxane pressure-sensitive adhesive, a rubber pressure-sensitive adhesive, a polyester pressure-sensitive adhesive, a polyester solvent adhesive, a rubber solvent adhesive. The water-based adhesive is preferably a water-based acrylic acid glue, or a polyurethane glue. The hot-melt adhesive can be an olefin hot melt adhesive, a polyurethane hot melt adhesive, a thermoplastic elastomer glue, a rubber adhesive, a polyester adhesive, a pressure sensitive adhesive, etc. The hot melt adhesive is preferably a polyurethane reactive glue, a polyester hot melt adhesive, an amide hot melt adhesive, an acrylic acid hot melt adhesive, etc.

Preferably, in the protective textile product of the present invention, the glue coated herein is non-continuous. The coating device can be any glue coating device, preferably a roller coating device, a spray coating device, a slit coating device, and powdering device, etc., and more preferably, a roller coating and spray coating device.

Preferably, in the protective textile product of the present invention, the bonding layer is a non-continuous layer so as to enhance the vapor permeation and moisture transmission performance of the laminate. More preferably, the bonding layer is a non-continuous dot layer, or a strip layer with bars or a grid layer.

The protective textile product of the present invention may be a bonded fabric comprising a vapor-permeable and virus-barrier thermoplastic elastomer film layer. It can also be a laminate in which a film lies between two fabric layers and the multiple layers are bonded with bonding layers. It can be a laminate with more layers. For laminates with multiple layers, the textile product used for bonding can be made of a plurality of materials, or a mixture thereof.

In the protective textile product of the present invention, the gram weight of the bonding layer is preferably from 0.8 to 50 g/m$^2$. The protective textile product of the present invention may be a medical textile product, preferably a garment such as a surgical garment or a consumable such as a surgical drape.

In the present invention, the vapor-permeable and virus-barrier thermoplastic elastomer film layer is a vapor-permeable film. When tested according to GB 12704.2, the moisture transmission rate is more than 3000 g/m$^2$*24 h, preferably more than 4000 g/m$^2$*24 h, more preferably more than 9000 g/m$^2$*24 h. The melting point is above 80 degrees Celsius, preferably above 98 degrees Celsius. By weight percentage, the components of the vapor-permeable and virus-barrier thermoplastic elastomer film layer comprises:

0.1%-99% thermoplastic elastomer resin, 0.01%-90% inorganic powder material having a grain diameter no more than 100 μm, and 0-5% dispersant, which is an organic material containing groups which are affinitive with resin.

The above film-making raw materials can be blended in machines, granulated after pre-blend melting, coated, or directly extruded to form films. Optimization is made according to different formulas. For instance, if it is organic low molecular formula, direct extrusion to form films is preferred. For the formula containing inorganic powders, however, it is preferable to pre-blend melting granulate and then to form the film. Film forming by extrusion may adopt multi-layer co-extrusion or single layer extrusion device. Preferably there is one to three layer extrusion. After that, the film is treated with intermediate special working processes such as surface treatment, solvent cleaning, printing, online ripening, and paint coating or adhesive coating, preferably with surface treatment, printing, sizing, and online ripening. Finally the resin film obtained is desirable and controllable in its mechanical properties, elasticity, toughness, dimensional stability, temperature range, optical properties and vapor permeability.

Herein below the present invention is further illustrated in combination with the drawings and embodiments. These embodiments, however, are only explanations or examples of some specific embodiments of the present invention, and shall not be construed as limitation of the present invention.

Numeral references in the above figures are as follows:
1: a fiber layer
2: glue layer
3: a vapor-permeable and virus-barrier film layer
4: a fiber layer.

It should be noted that the overlapping methods described in the above-mentioned drawings are only for the purpose of illustration and are not limitation of the present invention, and the present invention may also adopt other overlapping methods not limited thereto.

EMBODIMENTS

In the embodiments below, the gram weight (gram per square meter weight), seam crack resistance, softness, moisture transmission rate, hydrostatic pressure, blood barrier and virus barrier etc. are tested as follows:

(1) Standard for testing gram weight:
A) Testing device: analytical balance, precision 0.001 g;
B) Sampling standard: starting at 15 mm away from the widthwise edge, sampling every 60 mm widthwise, and sampling every 300 mm lengthwise; the testing sample size is 100×100 mm, and the number of samples taken from the widthwise and lengthwise is 100 pieces in total;

(2) Standard for testing peeling strength:
A) Testing standard: GB8808;
B) Sampling standard: starting at 15 mm away from the widthwise edge, sampling every 150 mm widthwise, and sampling every 500 mm lengthwise; the testing sample size is 15×180 mm, and the number of samples taken from the widthwise and lengthwise is 50 pieces in total;

(3) Seam crack resistance testing:
A) Testing standard: testing the seam strength by means of a steel pipe, pulling the steel pipe back and forth three times, then observing possible cracks of the seam;
B) Sampling standard: starting at 15 mm away from the widthwise edge, sampling every 150 mm widthwise, and sampling every 500 mm lengthwise; the testing sample size is 15×180 mm, and the number of samples taken from the widthwise and lengthwise is 50 pieces in total;

(4) Softness testing
A) Testing standard: ISO 17235;
B) Sampling standard: starting at 15 mm away from the widthwise edge, sampling every 150 mm widthwise, and sampling every 100 mm lengthwise; the testing sample size is 180×180 mm, and the number of samples taken from the widthwise and lengthwise is 10 pieces in total;

(5) Hydrostatic pressure testing standard
A) Testing standard: AATCC127;
B) Sampling standard: Take at least 3 pieces of samples in the size of 200 mm*200 mm diagonally, avoiding folding and contamination of the test area; before the test, the sample is humidified at (21±2) ° C., (65±2)% for at least 4 hours. The front side and back side of the fabric would be tested separately.
C) Testing method: At a temperature of (21±2) ° C., wipe dry the water on the surface of the clamping device, and then after humidifying the sample, clamp the sample so that its front side is in contact with the water surface. After that, select the test procedure, boost the pressure speed (60 mbar/min), record the water pressure value when the third drop of water appears; the three water drops should be different drops and not within 3 mm from the edge of the clamping device.

(6) Blood barrier testing standards
A) Testing standard: ASTM F 1670;
B) Sampling standards:
1. Randomly select 3 samples for each protective clothing material, based on conditions such as composition, portion of material (when a non-uniform material is designed) or other conditions.
2. If the protective clothing material has a seal layer sandwiched between the two fiber layers, the capillary effect at the edge of the material may result in false positives in the testing results, causing the samples to fail the test. In such cases, the edges of the test sample should be sealed to avoid possible capillary effects. The sample should be sealed with an adhesive, a sealant, a paraffin wax or a foam with a binder before the test.

3. Seal only the edge of the sample, leaving an open area of 57 mm in the sample center for testing.

4. If the sample is to be sterilized before it becomes a finished product, the sample should be disinfected. The disinfection process shall not hinder the performance of the sample and must meet the manufacturer's requirements.

5. The sample should be treated for at least 24 hours at a temperature of (21±5°) C. and a relative humidity of 30 to 80% before testing.

6. If possible, other pre-treatment processes (such as sterilization) are carried out to evaluate the performance of the protective clothing.

C) Testing method: The sample is subjected to a penetration test of simulated body fluid (synthetic blood) under a specified time and pressure (first at 0 kPa for 5 minutes, then at 13.8 kPa for 1 minute, and then at 0 kPa for 54 minutes). Penetration is then judged by the naked eye. Any evidence showing penetration of the synthetic blood indicates a failure in the blood barrier property of the sample. The result is "pass/fail".

(7) Virus barrier testing standard

A) Testing standard: ASTM F 1671;

B) Sampling standards:

1. Randomly select 3 samples for each protective clothing material, based on conditions such as composition, portion of material (when a non-uniform material is used) or other conditions.

2. If the protective clothing material has a seal layer sandwiched between the two fiber layers, the capillary effect at the edge of the material may result in false positives in the testing results, causing the samples to fail the test. In such cases, the edges of the test sample should be sealed to avoid possible capillary effects. The sample should be sealed with an adhesive, a sealant, a paraffin wax or a foam with a binder before the test.

3. Seal only the edge of the sample, leaving an open area of 57 mm in the center of the sample for testing.

4. If the sample is to be sterilized before it becomes a finished product, the sample should be disinfected. The disinfection process shall not hinder the performance of the sample and must meet the manufacturer's requirements.

5. The sample should be treated for at least 24 hours at a temperature of (21±5°) C. and a relative humidity of 30 to 80% before testing.

6. If possible, other pretreatment processes (such as sterilization) may be carried out to evaluate the performance of the protective clothing.

C) Testing method: The sample is subjected to the penetration test of the phage liquid Phi-X174 by using a specified support net, for a specified time and under a specified pressure (first 0 kPa for 5 minutes, then 13.8 kPa for 1 minute, then 0 kPa for 54 minutes). When no fluid permeation occurs, an analytical procedure is used to determine if the virus passes through the sample to the other side. If evidence shows a fluid or virus penetration occurs, it means the sample fails the test. The result is "pass/fail".

(8) Moisture transmission rate:

GB/T 12704.2 inverted cup testing (also known as hygroscopic testing) is carried out at a humidity rate of 90% and a temperature of 38° C.

Example 1

Figure 3:
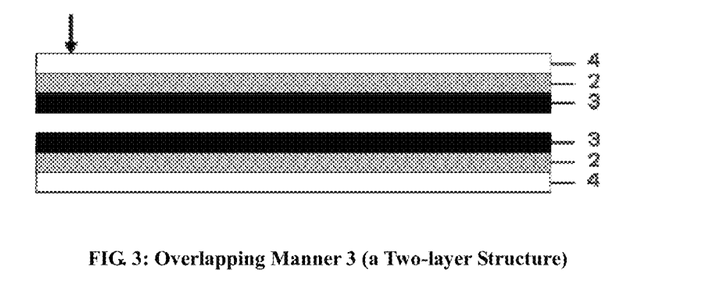
FIG. 3 shows an overlapping method for preparing a two-layer heat seal laminate according to an embodiment of the present invention.
Figure 4:
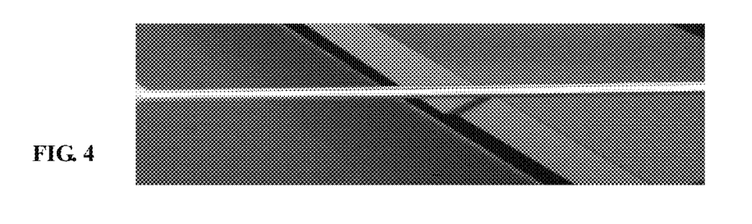
FIG. 4 is a tool for testing seam crack resistance according to the present invention.
Figure 5:
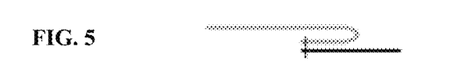
FIGS. 5-8 shows an overlapping method for preparing a three-layer heat seal laminate according to an embodiment of the present invention, in which a structure comprising a three-layer fabric is used.
Figure 6:
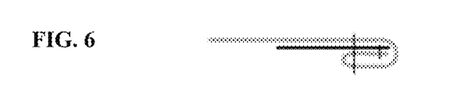
Figure 7:
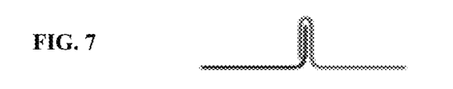
Figure 8:
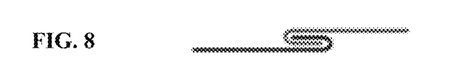

An 8 µm polyester derivative film having a melting point of 185 □ and a 23 g/m² PP non-woven fabric are dotted micro gravure bonded with a reactive liquid glue (or water-based glue), The glue has a gram weight of 3 g/m², the speed of the production line is 150 m/min, and then the bonded product is cooled, rolled up, and matured with glue. The product obtained is a two-layer fabric with a smooth surface and with no sticky touch. One film-side is disposed to face another film-side as shown in FIG. 3. Heat sealing is carried out for 3 seconds by means of a heat-sealing machine, at a temperature of 215° C. and under a pressure of 0.4 MPa. After the seam crack resistance test, the seam appears smooth and clean with the peeling strength reaching a point where the film would break. The test result of softness ISO 17235 is 3.0. The test result of moisture transmission rate GB/T 12704.2 is 14000 g/m²*24 h, and the hydrostatic test result is 140 mbar, and the test result of blood barrier ASTM F1670 is "pass" and the test result of virus barrier ASTM F 1671 is "pass". Two years of aging tracking shows that data remains above 80%, and the blood barrier and virus barrier test results are both "pass". This example demonstrates that heat sealing at this temperature causes the film to fuse, allowing the fabric to be fluid impervious and virus barrier while remaining wind-proof, vapor-permeable and water-proof.

Example 2

Figure 1:
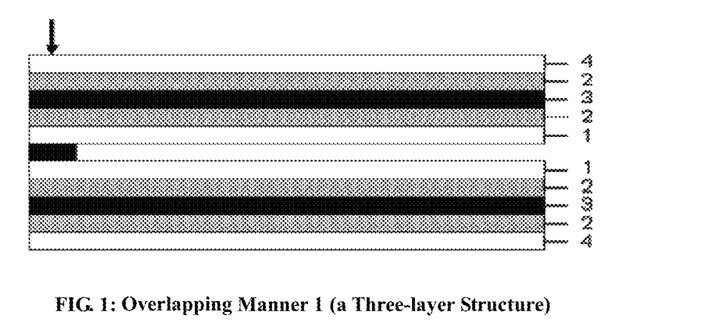
FIG. 1 shows an overlapping method for preparing a three-layer heat seal laminate according to an embodiment of the present invention.
Figure 2:
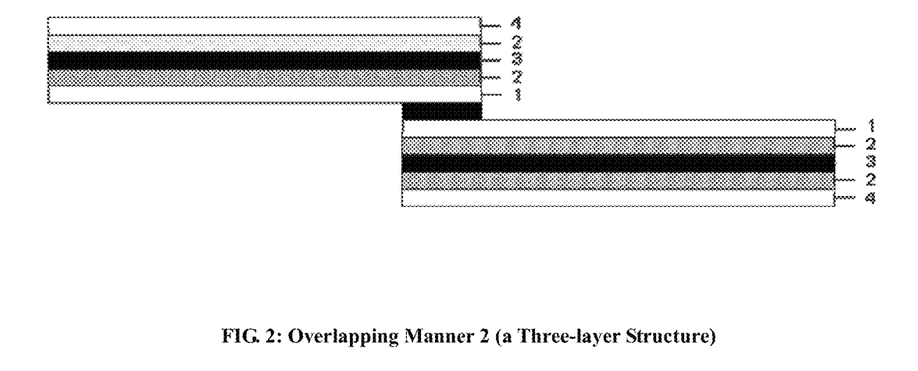
FIG. 2 shows an overlapping method for preparing a three-layer heat seal laminate according to another embodiment of the present invention.

The structure of Example 1 is used but bonded to a PP nonwoven fabric on the other side of the film. The glue has a gram weight of 3 g/m², the speed of the production line is 100 m/min, and the bonded product is cooled, rolled up, and matured with glue. The product obtained is a three-layer fabric with a smooth surface and with no sticky touch. Then any of the non-woven fabric is stacked as shown in FIG. 1. Heat sealing is carried out by means of a heat-sealing machine at a temperature of 215° C., other conditions being the same as Example 1. After the crack resistance test, the seam appears smooth and clean. The peeling strength reaches 32N/15 mm, the test result of softness ISO 17235 is 3.0, the test result of moisture transmission rate GB/T 12704.2 is 9500 g/m²*24 h, the hydrostatic test result is 130 mbar, the test result of blood barrier ASTM F1670 is "pass", and the test result of virus-barrier ASTM F 1671 is "pass". Two years of aging tracking shows that data remains above 80%, and the results of both the blood barrier and virus barrier tests are "pass". This example demonstrates that heat sealing at this temperature causes the three-layer material and the intermediate material to fuse, allowing the fabric to be fluid impervious and virus barrier while remaining wind proof, vapor-permeable and water proof. Adding one more layer of non-woven fabric does not hinder such a feature.

Example 3

A 25 µm polyester derivative film with a melting point of 212° C. and a 30 g/m² polyester fabric are dotted micro gravure bonded with reactive type hot melt polyurethane adhesive. Each side of the glue has a gram weight of 15 g/m². The speed of the production line is 20 m/min, and the bonded product is cooled, rolled up, matured with glue. The product obtained is a two-layer fabric with a smooth surface and with no sticky touch. Then one film-side is stacked to face another film-side as shown in FIG. 3. Heat sealing is carried out for 3 seconds by means of a heat-sealing machine, at a temperature of 215° C. and under a pressure of 0.4 MPa. The peeling strength reaches a point where the film would break. The test result of softness ISO 17235 is 3.0. The test result of moisture transmission rate GB/T 12704.2 is 5000 g/m²*24 h, the hydrostatic test result is 140 mbar, the test result of blood barrier ASTM F1670 is "pass", and the test result of virus-barrier ASTMF1671 is "pass". Two years of aging tracking shows that data remains above 80%, and the results of both the blood barrier and virus barrier tests are "pass". The test shows that the fabric is fluid impervious and virus-barrier while remains wind-proof, vapor-permeable and water proof. Such properties of the seam do not fail even after many times of washing.

Example 4

The gram weight of one layer of the non-woven fabric used in Example 2 is increased to 25 g/m², and then cooled, rolled up, matured with glue. The product obtained is a three-layer fabric with a smooth surface and with no sticky touch. Then one side of the non-woven fabric with a high gram weight is stacked over another side of the non-woven fabric also with a high gram weight. Heat sealing is carried out by means of a heat-sealing machine at a temperature of 215° C. After the crack resistance test, the seam appears smooth and clean. The peeling strength reaches 33N/15 mm. The test result of softness ISO 17235 is 2.8, the test result of moisture transmission rate GB/T 12704.2 is 9200 g/m²*24 h, the hydrostatic test result is 160 mbar, the test result of blood barrier ASTM F1670 is "pass", and the test result of virus-barrier ASTM F 1671 is "pass". Two years of aging tracking shows that data remains above 80%, and the results of both the blood barrier and virus barrier tests are "pass". This example demonstrates that the three-layer material is fused with the intermediate material at the above-mentioned temperature, and the increase in the gram weight of the nonwoven fabric increases the hydrostatic pressure at the seam.

Examples 5, 6, 7 and 8

One layer of the non-woven fabric used in Example 2 is changed to a pure polyester non-woven fabric with 30 g/m², and the other layer of the non-woven fabric remains a PP non-woven fabric with 23 g/m². The other conditions are the same as in Example 2. One polyester non-woven fabric is stacked on another polyester non-woven fabric, one PP non-woven fabric side is stacked facing another PP non-woven fabric side, and one side of the PP non-woven fabric is stacked facing one polyester non-woven fabric side. The pure polyester non-woven fabric is replaced with a polyester non-woven fabric containing the fused PP component, and this non-woven fabric and the PP non-woven fabric side are stacked as shown in FIG. 1. Heat sealing is carried out by means of a heat-sealing machine at a temperature of 260° C., 215° C., 260° C., 260° C. respectively. After the crack resistance test, the seam appears smooth and clean. The peeling strength reaches 35, 30, 15, 30N/15 mm respectively. The test result of softness ISO 17235 is 2.7, the test result of moisture transmission rate GB/T 12704.2 is 8900 g/m²*24 h, and the hydrostatic test result is 190, 140, 100, 139 mbar respectively. Except the PP non-woven fabric facing the polyester non-woven fabric side, the test results of blood barrier ASTM F1670 on the rest of the laminates are "pass". The test results of virus-barrier ASTM F 1671 are also"pass". Two years of aging tracking shows that data remains above 80%. The test results for blood and virus-barrier are both "pass". These examples demonstrate that when different non-woven materials having different melting points are heat sealed, it is necessary to ensure the mutual fusion among materials on the seam side; otherwise it would have some negative impacts on the peeling strength and the result of the barrier test on the heat sealing side.

Examples 9, 10, 11 and 12

The film of Example 2 is respectively replaced with a film of 10 μm, 12 μm, 20 μm, and 30 μm of the same melting point, in which the gram weight of the glue is respectively changed to 3 g/m², 3 g/m², 5 g/m², 6 g/m² to obtain a three-layer fabric with a smooth surface, and the non-woven fabric sides are stacked as shown FIG. 1. Heat sealing is carried out by means of a heat-sealing machine at a temperature of 215° C. After the crack resistance test, the seam appears smooth and clean. The peeling strength reaches 32 N/15 mm, 32.5 N/15 mm, 35 N/15 mm, and 38 N/15 mm, respectively. The test result of softness ISO 17235 is 3.0, 3.1, 3.1, 2.95, and 2.7, respectively; the test result of moisture transmission rate GB/T 12704.2 is 9200, 9000, 8500, and 7200 g/m²*24 h, respectively; the hydrostatic test result is respectively 140, 145, 165, and 190 mbar; the test results of blood barrier ASTM F1670 are "pass"; and the test results of virus-barrier ASTMF 1671 are "pass". Two years of aging tracking shows that data remains above 80%. The results of both the blood barrier and virus barrier tests are "pass". These examples demonstrate that the increase in film thickness does not affect the barrier performance of the heat seal of the fabric, but contributes greatly to its peeling strength and hydrostatic pressure. The moisture transmission rate decreases with the increase of the thickness.

Examples 13, 14, 15 and 16

The film of Example 2 is replaced respectively with a polyester film having a thickness of 10 μm and a melting point of 212° C., a polyester film having a thickness of 10 μm and a melting point of 220° C., a nylon film having a thickness of 10 μm and a melting point of 160° C., and a nylon film having a thickness of 10 μm and a melting point of 135° C., thus obtaining a three-layer fabric with a smooth surface. The non-woven fabric sides are stacked as shown in FIG. 1. Heat sealing is carried out by means of a heat-sealing machine at a temperature of 220° C., 225° C., 175° C., and 170° C., respectively. After the crack resistance test, the seam appears smooth and clean. The peeling strength reaches 30 N/15 mm, 34 N/15 mm, 29 N/15 mm, and 28 N/15 mm, respectively; the test result of softness ISO 17235 is 3.0, 3.1, 3.7, and 3.9, respectively; the test result of moisture transmission rate GB/T 12704.2 is 9500, 9300, 9350, and 8000 g/m²*24 h, respectively; the hydrostatic test result is 140, 145, 125 mbar, and 120 mbar, respectively; the test results of blood barrier ASTM F1670 are "pass"; and the test results of virus-barrier ASTMF 1671 are also"pass". Two years of aging tracking shows that data remains above 80%. The results of both the blood barrier and virus barrier tests are "pass". These examples demonstrate that when the melting point of the film is higher than that of the non-woven fabric, the heat sealing temperature should be higher than the melting point of the film. When the melting point of the film is lower than that of the non-woven fabric, the heat sealing temperature should be higher than or equal to the non-woven fabric. In this way, the heat seal strength and the barrier performance of the seal is guaranteed.

Examples 17, 18, 19 and 20

The film of Example 2 is replaced with a polyester film with a higher strength and a melting point of 195 degrees Celsius, or the non-woven fabric is replaced with a 23 g/m² PP non-woven fabric with a higher strength, or the amount of glue is changed to 0.5 g/m² and 5 g/m². The other conditions are the same as Example 2, and thereby a smooth three-layer fabric is obtained, and the non-woven fabric sides are stacked as shown in FIG. 1. Heat sealing is carried out by means of a heat-sealing machine at a temperature of 215° C. After the crack resistance test, the seam appears smooth and clean. The peeling strength reaches 33, 35, 23, and 35 N/15 mm, respectively; the test result of softness ISO 17235 is 2.9, 2.7, 3.3, and 2.9, respectively; the test result of moisture transmission rate GB/T 12704.2 is 5000, 9200, 12000, and 8000 g/m²*24 h; and the hydrostatic test result is 139, 156, 105, and 215 mbar respectively. Except the 1 g/m² glue samples in which only ⅔ of the samples pass the test of blood barrier ASTM F1670, the other samples all pass the test. The test results of virus-barrier ASTM F 1671 are "pass". Two years of aging tracking shows that data remains above 80%. The results of both the blood barrier and virus barrier tests are "pass". These examples demonstrate that increasing the strength of each base material contributes to both the barrier performance and the peeling strength of the heat-stitched seam; if the strengths of these materials are too weak, it would result in instability of performance.

Examples 21, 22 and 23

The three-layer fabric of Example 2 is heat sealed by means of a heat-sealing machine at a temperature of 205° C., 210° C., 220° C., 225° C., respectively. After the crack resistance test, the seam appears smooth and clean. The peeling strength reaches 29 N/15 mm, 33.5 N/15 mm, 34 N/15 mm, and 34.9 N/15 mm, respectively; the test result of moisture transmission rate GB/T 12704.2 is 9200 g/m²*24 h; the hydrostatic test result is 120, 140.
190, and 230 mbar respectively; the test results of blood barrier ASTM F1670 are "pass"; and the test results of virus-barrier ASTM F 1671 are "pass". Two years of aging tracking shows that data remains above 80%. The results of both the blood barrier and virus barrier tests are "pass". These examples demonstrate that the increase in heat sealing temperature within a certain range contributes to a significant improvement in barrier performance, peeling strength and hydrostatic pressure of the heat seal of the fabric.

Examples 24, 25 and 26

The three-layer fabric of Example 2 is heat sealed by means of a heat-sealing machine at a temperature of 215° C. under a pressure of 0.05, 0.6, and 1.2 MPa, respectively. After the crack resistance test, the seam appears smooth and clean. The peeling strength reaches 10 N/15 mm, 34 N/15 mm, 40 N/15 mm, and 38N/15 mm, respectively. The hydrostatic test result is 60, 160, and 50 mbar respectively. Only the sample under the pressure of 0.6 MPa passes the test of blood barrier ASTM F1670, and also only the sample under the pressure of 0.6 MPa passes the test of virus-barrier ASTM F 1671. These examples demonstrate that the increase in heat-sealing pressure contributes to the improvement of the barrier performance and heat-sealing strength of the heat seal of the fabric to a certain degree, but if the pressure is too high, it would result in perforation of the vapor-permeable barrier layer, which is a negative effect. If the pressure is too low, the material would not be effectively fused with the woven fabric, and likewise it would also have a negative effect on the barrier performance and heat sealing strength.

The invention claimed is:

1. A stitching method for making a fluid impervious seam at a vapor-permeable and virus-barrier laminate used in a protective textile product, wherein the laminate comprises a plurality of material layers:
   at least one thermoplastic resin fiber layer with a gram weight of 5-200 g/m²;
   at least one thermoplastic elastomer film layer with a thickness of 4-100 μm which is vapor-permeable and virus-barrier; and
   a bonding layer formed between the thermoplastic resin fiber layer and the thermoplastic elastomer film layer by a glue which is fused with the thermoplastic resin fiber layer and the thermoplastic elastomer film layer with a gram weight of 0.1 g/m² or more
   wherein, in said stitching method for forming a seam of a laminate, the part of the laminate to form a seam is overlapped or stacked to, and then is heat-sealed; wherein, the temperature of heat sealing is higher than or equal to the highest melting point of the material layers in the laminate, but lower than the temperature at which perforation or decomposition occurs in any material layer in the laminate, wherein the heat sealing is conducted by performing thermal press at the overlapped or stacked portion of the laminate by means of a heat-stitching device to form a suture, in which the heat sealing is conducted at a pressure of 0.001 to 1 MPa with a time of 1 to 480 s.

2. The stitching method according to claim 1, wherein the heat sealing causes all material layers to experience a certain extent of melting.

3. A protective textile product in which a vapor-permeable and virus-barrier laminate is used and the stitching method of claim 1 is used to form a fluid impervious seam at the stitched portion of the laminate, wherein the laminate comprises:
   at least one thermoplastic resin fiber layer with a gram weight of 5-200 g/m²;
   at least one thermoplastic elastomer film layer with a thickness of 4-100 μm which is vapor-permeable and virus-barrier; and
   a bonding layer formed between the thermoplastic resin fiber layer and the thermoplastic elastomer film layer by a glue which is fused with the thermoplastic resin fiber layer and the thermoplastic elastomer film layer with a gram weight of 0.1 g/m² or more,
   wherein, in said stitching method for forming a seam of a laminate, the part of the laminate to form a seam is overlapped or stacked to, and then is heat-sealed; wherein, the temperature of heat sealing is higher than or equal to the highest melting point of the material layers in the laminate, but lower than the temperature at which perforation or decomposition occurs in any material layer in the laminate, and the heat sealing is conducted by performing thermal press at the overlapped or stacked portion of the laminate by means of a heat-stitching device to form a suture, in which the heat sealing is conducted at a pressure of 0.001 to 1 MPa with a time of 1 to 480 s.

4. The protective textile product according to claim 3, wherein the thermoplastic resin fiber layer is selected from a group consisting of: fibers of polyester and its derivatives, fibers of polyamide and its derivatives, fibers of polyimide and its derivatives, fibers of polyurethane and its derivatives, fibers of polypropylene and its derivatives, fibers of polyethylene and its derivatives, fibers of polyvinyl alcohol and its derivatives, fibers of polyacrylonitrile and its derivatives, bio-based fibers, degradable fibers and their derivatives, and a textile product made of mixtures thereof.

5. The protective textile product according to claim 3, wherein the thermoplastic elastomer film layer is selected from a group of a thermoplastic elastomer plastic and its derivatives and mixtures consisting of: polyvinyl acetate and its derivatives and mixtures, polyvinyl chloride and its derivatives and mixtures, polyvinyl alcohol and its derivatives and mixtures, polyethylene terephthalate and its derivatives and mixtures, and polybutylene terephthalate and its derivatives and mixtures, polyamide and its derivatives, amino resin and its derivatives and mixtures, unsaturated polyester resin and its derivatives and mixtures, epoxy resin and its derivatives and mixtures, and organic silicone resin and its derivatives and mixtures.

6. The protective textile product according to claim 3, wherein the gram weight of the bonding layer is from 0.8 to 50 $g/m^2$, and the bonding layer is a non-continuous layer.

7. The protective textile product according to claim 6, wherein the non-continuous layer for the bonding layer is selected from a non-continuous dot layer, strip layer, or grid layer.

8. The protective textile product according to claim 3, wherein the protective textile product is a garment or a consumable.

* * * * *